(12) United States Patent
Jefferson et al.

(10) Patent No.: US 6,849,660 B1
(45) Date of Patent: Feb. 1, 2005

(54) ANTIMICROBIAL BIARYL COMPOUNDS

(75) Inventors: Elizabeth Jefferson, La Jolla, CA (US); Eric Swayze, Carlsbad, CA (US)

(73) Assignee: ISIS Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 09/630,122

(22) Filed: Aug. 1, 2000

(51) Int. Cl.[7] .................... A61K 31/445; A61K 31/44; A61K 31/40; A61K 31/34; C07D 335/00; C07D 307/02; C07D 315/00; C07D 333/32; C07D 333/36

(52) U.S. Cl. .................... 514/471; 514/249; 514/252.2; 514/252.13; 514/252.16; 514/253.04; 514/254.1; 514/263.23; 514/266; 514/274; 514/326; 514/343; 514/422; 544/264; 544/265; 544/274; 544/276; 544/277; 544/295; 544/354; 544/362; 544/379; 546/208; 546/278.4; 548/517; 549/13; 549/28; 549/63; 549/65; 549/419; 549/424; 549/425; 549/426; 549/479; 549/480; 549/483; 549/487

(58) Field of Search ................... 544/295, 264, 544/379, 310, 265, 354, 362, 276, 277; 514/252.2, 266, 422, 252.13, 471, 274, 326, 252.16, 249, 253.04, 254.1, 263.23, 343; 548/517; 546/208, 278.4; 549/487, 13, 28, 63, 65, 419, 424, 425, 426, 479, 480, 483

(56) References Cited

FOREIGN PATENT DOCUMENTS

WO   WO 96/10559   4/1996

OTHER PUBLICATIONS

A.L. Lehninger, Principles of Biochemistry, Worth Publishers, New York, 1985; ISBN 0–87901–136–X.*
J.S. Davis (Ed.), Amino Aciids and Peptides, Chapman and Hall, New York, 1985; ISBN 0–412–26950–3.*
Marchbanks, C. et al., "New Fluoroquinolones", *Hospital Therapy*, 1988, 7, 18–19, 23–27, 31, and 34–35.
Parry, M., "Pharmacology and Clinical Uses of Quinolone Antibiotic", *Medical Times*, 1988, 116(12), 39–45 and 19.
Shah, P., "Quinolones", *Prog. Drug Res.*, 1987, 31, 243–256.
Ehmer et al., "Development of a Simple and Rapid Assay for the Evaluation of Inhibitors of Human 17.alpha.–hydroxylase–C17,20–lyase (P450c17), by Coexpression of PH450c17 with NADPH–cytochrome–P450–reductase in *Escherichia coli*," *Journal of Steroid Biochemistry & Molecular Biology*, Dec. 2000, 75,(1), 57–63.

Gravel et al., "Resin–to–Resin Suzuki Coupling of Solid Supported Arylboronic Acids," *Journal of Combinatorial Chemistry*, May 2000, 2(3), 228–231.

Search Report issued in International Application No. PCT/US01/24067, Date of Mailing: Apr. 3, 2002.

Copy of PCT Written Opinion dated Feb. 24, 2003 (PCT/US01/24067).

Muller, et al., "Polyamide oligomers from epsilon–aminocaproic acid and isomeric aminophenylcarboxylic acids," *J. for Praktische Chemie*, 1970, 312(1), 78–89.

* cited by examiner

*Primary Examiner*—Brenda Coleman
(74) *Attorney, Agent, or Firm*—Michael P. Straher; Cozen O'Connor

(57) ABSTRACT

Provided are antibacterial compounds having Formula I:

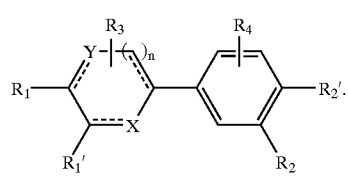

In such compositions, X is O or S; Y is $CH_2$; n is 0 or 1. One of $R_1$ and $R_{1'}$ is —C(O)$NR_5R_{5'}$, —C(O)—Q—$NR_5R_{5'}$, —$CH_2NR_5R_{5'}$, or —S(O)$_2NR_5R_{5'}$ and the other is H or $R_3$. One of $R_2$ and $R_{2'}$ is —NHC(O)$R_6$ or —NHS(O)$_2R_6$ and the other is H or $R_4$. Q is an amino acid or peptide. $R_3$ is H, halogen, —$NR_5R_{5'}$ or —NHC(O)$R_6$; and $R_4$ is selected from the group consisting of H, halogen, hydroxyl, amino, carboxyl, alkyl, alkenyl and alkynyl. $R_5$ is selected from the group consisting of H, alkyl, alkenyl or alkynyl optionally substituted with halogen, OH, amino, amidinyl, guanidinyl, urea, alkyl, carboxyl, oxo, carboxamide; $R_{5'}$ is H or $R_5$ and $R_{5'}$ together form a 5–16 member heterocycle optionally substituted with halogen, OH, amino, alkyl, carboxyl, carbonyl or carboxamide. $R_6$ is selected from the group consisting of H; amino; alkyl, alkenyl or alkynyl, each optionally substituted with halogen, amino, amidinyl, guanidinyl, urea, carboxyl or carboxamide; a 5–16 member carbocycle or heterocycle; and a 5–16 member heterocycle-substituted alkyl or carbocycle-substituted alkyl, wherein said carbocycle and heterocycle are optionally substituted with halogen, OH, amino, alkyl, carboxyl, oxo or carboxamide.

2 Claims, No Drawings

ANTIMICROBIAL BIARYL COMPOUNDS

FIELD OF THE INVENTION

The present invention relates to novel biaryl compounds useful as therapeutic agents, and in particular to biphenyl compounds having antimicrobial activity.

BACKGROUND OF THE INVENTION

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring (antibiotic), synthetic, or semi-synthetic compounds. They may be classified as aminoglycosides, ansamacrolides, beta-lactams (including penicillins and cephalosporins), lincosaminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in Antibiotics, Chemotherapeutics, and Antibacterial Agents for Disease Control (M. Grayson, editor, 1982), and E. Gale et al., The Molecular Basis of Antibiotic Action 2d Edition (1981).

The mechanisms of action of these antibacterials vary. However they can generally be classified as functioning in one of the following ways. Antibacterials may function by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. On the other hand, quinolones act by inhibiting synthesis of bacterial DNA, thus preventing the bacteria from replicating.

Not surprisingly, the pharmacological characteristics of antibacterials and other antimicrobials, as well as their suitability for a specific clinical use, varies considerably. For example, the classes of antimicrobials (and members within a class) may vary in their relative efficacy against different types of microorganisms and their susceptibility to development of microbial resistance. These antimicrobials may also differ in their pharmacological characteristics, such as their bioavailability, and biodistribution. Accordingly, selection of an appropriate antibacterial (or other antimicrobial) in any given clinical situation can be a complicated analysis of many factors, including the type of organism involved, the desired method of administration, and the location of the infection to be treated.

The pharmaceutical literature is replete with attempts to develop improved antimicrobials (i.e., compounds that have a broader scope of activity, greater potency, improved pharmacology, and/or less susceptibility to resistance development.) One group of antimicrobials recently developed for clinical use is the quinolones. These compounds include, for example, nalidixic acid, difloxacin, enoxacin, fleroxacin, norfloxacin, lomefloxacin, ofloxacin, ciprofloxacin, and pefloxacin. See, C. Marchbanks and M. Dudley, "New Fluoroquinolones," 7 Hospital Therapy 18 (1988); P. Shah, "Quinolones," 31 Prog. Drug Res. 243 (1987); Quinolones—Their Future in Clinical Practice, (A. Percival, Editor, Royal Society of Medical Services, 1986); and M. Parry, "Pharmacology and Clinical Uses of Quinolone Antibiotics," 116 Medical Times 39 (1988).

However, many such attempts to produce improved antimicrobials have produced equivocal results. For example, the quinolones often show reduced effectiveness against certain clinically important pathogens, such as gram positive bacteria and/or anaerobic bacteria. The quinolones also have limited water solubility limiting their bioavailability and suitability for parenteral dosing. They may also produce adverse side effects, such as gastrointestinal disturbance and central nervous system effects such as convulsions. Accordingly there remains a need for new effective antimicrobial compounds.

SUMMARY OF THE INVENTION

According to an aspect of the present invention there is provided compounds of formula (I):

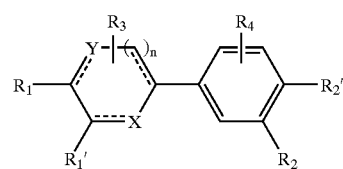

wherein X is CH, O, S, N or NH;

Y is CH or N;

n is 0 or 1;

one of $R_1$ and $R_{1'}$ is —C(O)NR$_5$R$_{5'}$, —C(O)—Q—NR$_5$R$_{5'}$, —CH$_2$NR$_5$R$_{5'}$ or —S(O)$_2$NR$_{5'}$ and the other is H or $R_3$;

one of $R_2$ and $R_{2'}$ is —NHC(O)R$_6$ or —NHS(O)$_2$R$_6$ and the other is H or $R_4$;

Q is an amino acid or peptide;

$R_3$ is H, halogen, —NR$_5$R$_{5'}$ or —NHC(O)R$_6$;

$R_4$ is selected from the group consisting of H, halogen, hydroxyl, amino, carboxyl, alkyl, alkenyl, alkynyl, alkoxy, a carbocycle and a heterocycle.

$R_5$ is selected from the group consisting of H, alkyl, alkenyl, alkynyl, a carbocycle, and a heterocycle, each of which is optionally substituted with halogen, OH, amino, amidinyl, guanidinyl, urea, carboxyl, oxo or carboxamide;

$R_{5'}$ is H or $R_5$ and $R_{5'}$ together form a heterocycle optionally substituted with halogen, OH, amino, alkyl, carboxyl, carbonyl or carboxamide; and $R_6$ is selected from the group consisting of H; amino; alkyl, alkenyl or alkynyl, each optionally substituted with halogen, amino, amidinyl, guanidinyl, urea, carboxyl or carboxamide; a carbocycle; a heterocycle; a heterocycle-substituted hydrocarbyl group; and a carbocycle-substituted hydrocarbyl group, wherein said carbocycle and heterocycle are optionally substituted with halogen, OH, amino, alkyl, carboxyl, oxo or carboxamide; and salts, solvates and hydrates thereof.

In another aspect of the invention there is provided a method of treating bacterial infection in a mammal comprising administering to said mammal an effective amount of a biaryl compound of the invention.

DETAILED DESCRIPTION OF THE INVENTION

Biaryl compounds are provided having therapeutic activity, in particular antibacterial activity having the general formula (I)

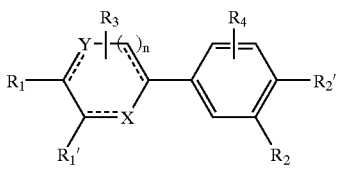

I

The dashed bonds in the left ring signify that double bonds may occur at various places within the ring, depending on the number of atoms present in the ring. For example, one skilled in the art will recognize that in a 5-membered aromatic ring only 2 double bonds will be present in the ring, while in a 6-membered ring, 3 double bonds will be present.

According to the present invention, X is CH, O, S, N or NH; Y is CH or N; and n is either 0 or 1. X, Y and n are selected such that the ring is aromatic. In a preferred embodiment, X and Y are both CH and n is 1, thereby forming a benzene ring. In another preferred embodiment X is S, Y is CH and n is 0, thereby forming a thiophene ring. In another preferred embodiment X is S, Y is N and n is 0, thereby forming a thiazole ring. In another preferred embodiment X is O, Y is CH and n is 0, thereby forming a furan ring. In another preferred embodiment X is CH, Y is N and n is 1, thereby forming a pyridine ring. In another preferred embodiment X is N, Y is CH and n is 1, or X is CH, Y is N and n is 1 thereby forming pyridine rings.

One of $R_1$ and $R_{1'}$ is the group —C(O)NR$_5$R$_{5'}$, —C(O)—Q—NR$_5$R$_{5'}$, —CH$_2$NR$_5$R$_{5'}$, or —S(O)$_2$NR$_5$R$_{5'}$, while the other is H or $R_3$. In a preferred embodiment, $R_1$ is —C(O)NR$_5$R$_{5'}$ and $R_{1'}$ is H. In another preferred embodiment, $R_1$ is —C(O)—Q—NR$_5$R$_{5'}$ wherein Q is a natural or unnatural amino acid residue or a peptide or peptidomimetic, preferably 2 to 4 residues in length. Unnatural amino acids include β-amino acids such as β-alanine. The alpha nitrogen of the amino acid (or N-terminus of the peptide) forms an amide bond to the —C(O) portion of the group while the carboxyl carbon (or C-terminus of the peptide) forms an amide bond to the NR$_5$R$_{5'}$ portion of the group. In a preferred embodiment Q is an amino acid selected from the group consisting of lysine, arginine, histidine, glutamine, asparagine, serine and tyrosine. In another preferred embodiment Q is an amino acid having a side chain of selected from the group consisting of H, alkyl, hydroxylalkyl, aminoalkyl, guanidinylalkyl, aminocarbonylalkyl, aryl, aralkyl, amino substituted aralkyl, hydroxyl substituted aralkyl.

$R_5$ is selected from the group consisting of H; a hydrocarbyl group such as alkyl, alkenyl, alkynyl, a carbocycle; or a heterocycle. The hydrocarbyl or heterocyclic group is optionally substituted with one or more of the following groups: carbocycle, preferably cycloalkyl or aryl, heterocycle, preferably heteroaryl, halogen, preferably F or Cl, OH, amino (—N(R)$_2$), amidinyl (—C(NH)—N(R)$_2$ or —NH—C(NH)—R), guanidinyl (—NH—C(NH)—NHR), urea (—NH—C(O)—NHR), alkyl, carboxyl (—COOR), oxo (=O), and carboxamide (—C(O)NHR) wherein R is H or a hydrocarbyl group. In a preferred embodiment, $R_5$ is H, alkyl, aryl, or heteroaryl. In a particularly preferred embodiment $R_5$ is H.

$R_{5'}$ is H or $R_5$ and $R_{5'}$ together form a heterocycle optionally substituted with one or more halogen, OH, amino, alkyl, carboxyl, carbonyl or carboxamide substituents. In a preferred embodiment, $R_{5'}$ is H and, more preferred, both $R_5$ and $R_{5'}$ are H. In another preferred embodiment $R_5$ and $R_{5'}$ together form a 5-6 member nitrogen containing heterocycle which is optionally substituted. A preferred heterocycle includes piperazine, and pyrrolidine. In a preferred embodiment the pyrrolidine is substituted at the 2-position with a carboxamide group (—C(O)NH$_2$) and at the 4-position with hydroxyl (i.e. 2-carboxamide-4-hydroxy-pyrrolidine).

One of $R_2$ and $R_{2'}$ is —NHC(O)R$_6$ or —NHS(O)$_2$R$_6$ and the other is H or $R_4$. In a particular embodiment, $R_2$ is —NHC(O)R$_6$ while $R_{2'}$ is H or $R_4$.

$R_6$ is selected from the group consisting of H; amino; alkyl, alkenyl or alkynyl, each optionally substituted with halogen, amino, amidinyl, guanidinyl, urea radical, carboxyl, or carboxamide radical; a carbocycle; a heterocycle; a heterocycle-substituted hydrocarbyl group; and a carbocycle-substituted hydrocarbyl group. The carbocycle and heterocycle are optionally substituted with halogen, OH, amino, alkyl, carboxyl, oxo or carboxamide. In a preferred embodiment, $R_6$ is a carbocycle, heterocycle, carbocycle-substituted alkyl or heterocycle-substituted alkyl wherein said carbocycle and heterocycle are optionally substituted with alkyl, amino, guanidinyl, hydroxyl or oxo. In a preferred embodiment, $R_6$ is amino or alkyl optionally substituted with hydroxyl, amino, amidinyl guanidinyl or urea. More preferably, R6 is aminomethyl hydroxyethyl, ureamethyl or 1-amino-2-hydroxyethyl. In another preferred embodiment, $R_6$ is selected from the group consisting of

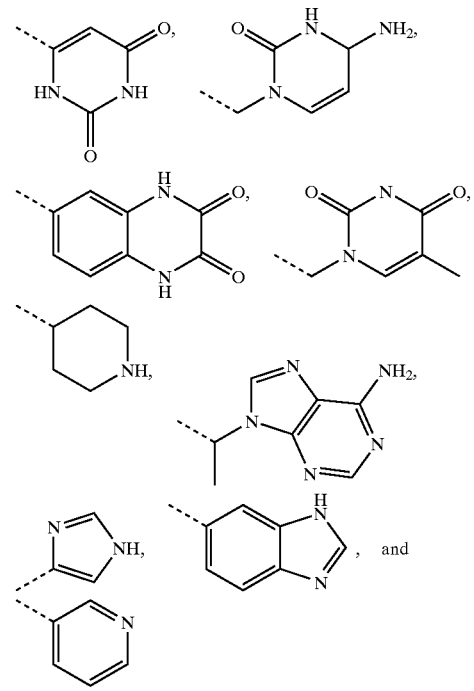

$R_3$ is H, halogen, —NR$_5$R$_{5'}$ or NHC(O)R$_6$ wherein R$_5$, R$_{5'}$ and R$_6$ are as previously defined.

In a preferred embodiment, $R_3$ is —NR$_5$R$_{5'}$ wherein one of $R_5$ and $R_{5'}$ is H and the other is selected from the group consisting of H and alkyl optionally substituted with amino, hydroxyl or urea. In the context of $R_3$, a particularly preferred embodiment is when one of $R_5$ and $R_{5'}$ is H and the other is aminomethyl, hydroxymethyl, or ureamethyl (—CH$_2$—NH—C(O)—NH$_2$).

In another embodiment, $R_3$ is —NHC(O)R$_6$ wherein R$_6$ is selected from the group consisting of H; amino; alkyl, alkenyl or alkynyl. The alkyl, alkenyl and alkynyl groups are optionally substituted with one or more halogen, amino, amidinyl, guanidinyl, urea, carboxyl or carboxamide groups. In this context $R_6$ is preferably aminomethyl, hydroxyethyl, ureamethyl or 1-amino-2-hydroxyethyl. In an alternative embodiment, $R_3$ is —NHC(O)$R_6$ wherein $R_6$ is a 5 to 16 member nitrogen containing heterocycle or heterocycle-substituted alkyl. The heterocycle is optionally substituted with $C_{1-4}$ alkyl, amino and oxo. In a particularly preferred embodiment, $R_3$ is —NHC(O)$R_6$ and $R_6$ is a nucleobase or a nucleobase substituted $C_{1-4}$ alkyl. In another particularly preferred embodiment, $R_3$ is —NHC(O)$R_6$ and $R_6$ is selected from the group consisting of

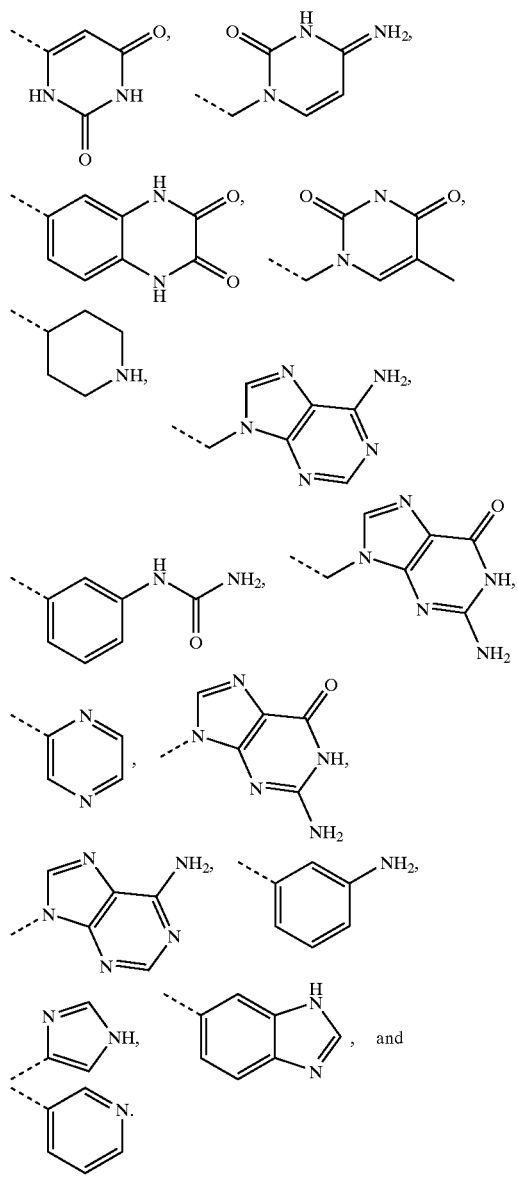

$R_4$ is selected from the group consisting of H, halogen, hydroxyl, amino, carboxyl, alkyl, alkenyl, alkynyl, alkoxy, a carbocycle and a heterocycle. In a preferred embodiment, $R_4$ is H.

"Hydrocarbyl" groups are aliphatic or carbocyclic groups. Aliphatic hydrocarbyl groups according to the invention include saturated (i.e., alkyl) and unsaturated (i.e., alkenyl and alkynyl) which are straight or branched chains having from 1 to about 12 carbon atoms in length, and preferably 1-6 carbons and most preferably 1-4 carbons, e.g., methyl, ethyl, propyl, i-propyl, butyl, i-butyl, s-butyl and t-butyl. "Carbocyclic" hydrocarbyl groups include 3 to about 16 membered, mono-, bi- or tricyclic carbon ring systems which are saturated or unsaturated. Preferred carbocyclic groups include cycloalkyl (e.g. cyclopropyl, cyclobutyl, cyclopentyl and cyclohexyl) and aryl (e.g., phenyl, naphthyl, anthracenyl and phenanthrenyl). "Heterocycles" include 5 to about 16 membered, mono-, bi- or tricyclic ring systems which may be saturated (including heteroaryl) or unsaturated and contain at least one heteroatom (e.g., N, O, S, SO, $SO_2$) in at least one ring of the ring system. Preferred heterocycles include piperidine, piperazine, pyridine, pyrazine, pyrimidine, pyrrolidine, pyrrole, imidazole, pyrazole, quinoline, isoquinoline, naphthyridine, indole, purine, carbazole, morpholine, furan, pyran and thiophene. The heterocycle is attached via a covalent bond to either a heteroatom or a carbon atom of the ring system. It will be appreciated by the skilled artisan that attachment depends on the particular heterocycle and group from which it depends.

It will be appreciated that compounds of the invention may incorporate chiral centers and therefore exist as geometric and stereoisomers. All such isomers are contemplated and are within the scope of the invention whether in pure isomeric form or in mixtures of such isomers as well as racemates.

Compounds of the invention may be prepared according to established organic synthetic techniques from starting materials and reagents that are commercially available. In a particular embodiment, biaryl compounds of the invention are prepared by coupling the two aryl moieties, an A ring and a B ring, as shown in Scheme 1.

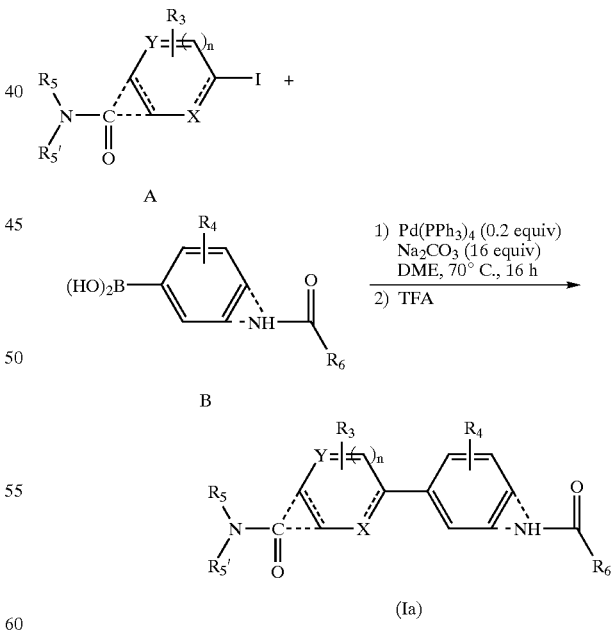

Referring to Scheme 1, coupling may be achieved by a Suzuki reaction wherein an iodo or bromo derivatized A or B ring is reacted with the other of the A or B ring which is derivatized with a boronic acid substituent. The reaction occurs in the presence of a typical Suzuki reaction catalyst such as tetrakis-triphenylphosphine palladium (Pd(PPh$_3$)$_4$)

and in a polar solvent such as ethyleneglycol dimethyl ether (DME) at elevated temperature (about 70° C.) over several hours, wherein the boronic acid ring intermediate is provided in molar excess (about 7 equivalents) relative to the iodo ring intermediate.

The coupling of the A and B ring will yield final compound of formula (Ia), wherein $R_3$, $R_4$, $R_5$, $R_{5'}$ and $R_6$ are as previously defined. It will be appreciated by those skilled in the art of organic chemistry that, depending on the structure of the substituents $R_3$, $R_4$, $R_5$, $R_{5'}$ and $R_6$, protection and deprotection steps may be necessary to achieve the desired compound of the invention. Suitable protecting groups and their preparation are described in detail in Greene and Wuts (Protective Groups in Organic Chemistry, 2d edition, John Wiley and Sons, 1991)* herein incorporated by reference. For example, suitable amine protecting groups include t-butyloxycarbonyl (Boc), fluorenyl-methyloxycarbonyl (Fmoc), 2-trimethylsilyl-ethyoxycarbonyl (Teoc), 1-methyl-1-(4-biphenylyl)ethoxycarbonyl (Bpoc), allyloxycarbonyl (Alloc), and benzyloxycarbonyl (Cbz). Suitable carboxyl protecting groups include alkyl esters such as acetyl (Ac), methoxymethyl (MOM), methylthiomethyl (MTM), terahydropyranyl (TMP), methoxyethoxymethyl (MEM) and benzyloxymethyl (BOM).

Compounds of the invention may also be prepared by first coupling the A and B rings as previously described and subsequently appending the desired substituents defined by $R_3$, $R_4$, $R_5$, $R_{5'}$ and $R_6$. For example, a carboxyl substituted A ring may be coupled to an amino substituted B ring as shown in Scheme 2.

One of the carboxyl or amino groups on the A and B rings is preferably protected prior to the Suzuki coupling of the rings. Following coupling, the free amine or carboxyl group may then be acylated with a group $R_6$—C(O)OH or $HN(R_5)_2$ respectively.

Alternatively, compounds of the invention may be prepared using solid phase techniques wherein a substituent group of the compound is bound to a solid support (resin) and reacted with appropriate reagents to arrive at the final compound. For example, a carboxyl substituted A ring may be bound to an amine-derivatized support by formation of an amide bond. The A ring could then be subjected to Suzuki coupling reaction with a B ring as shown in Scheme 3.

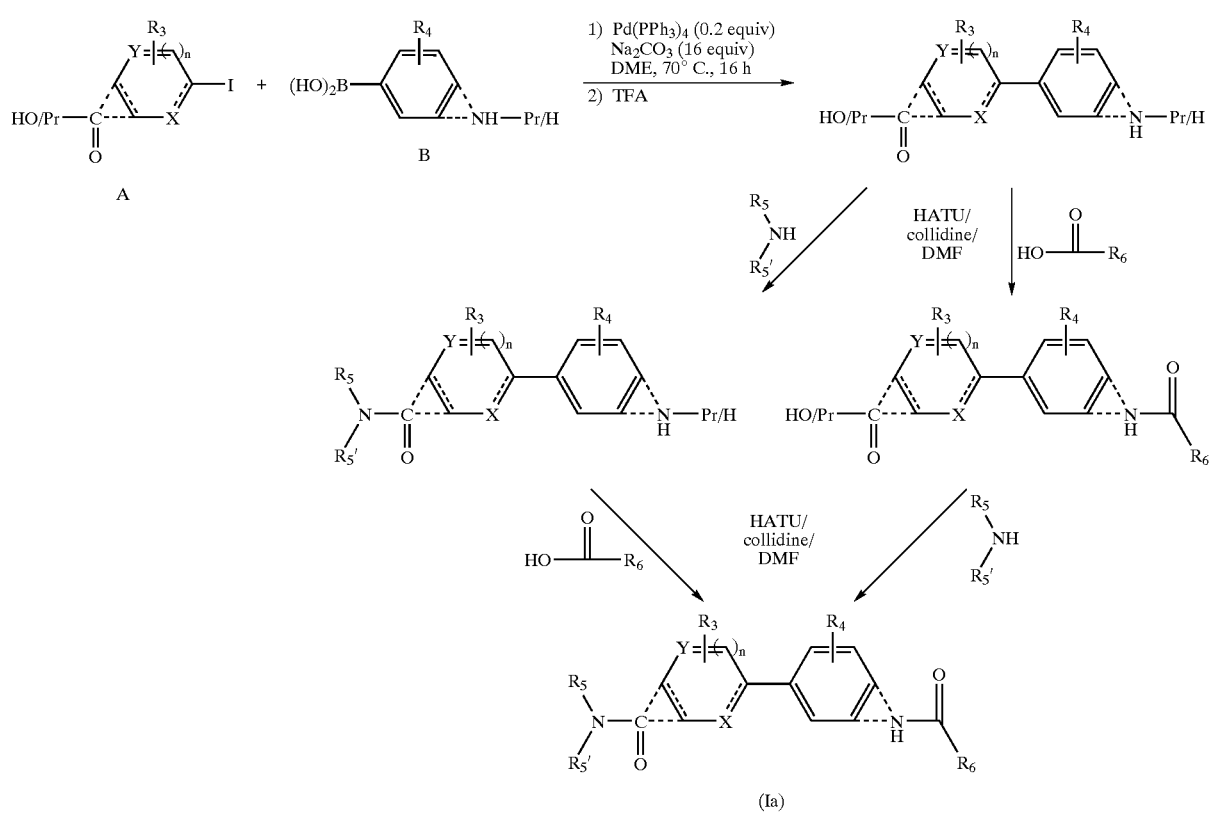

Scheme 3
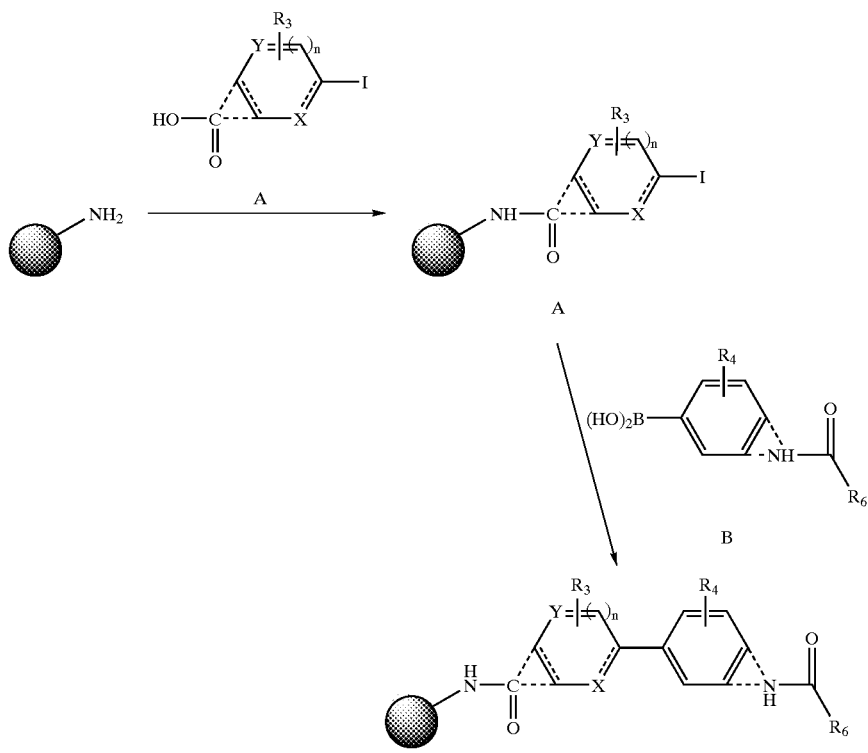
The bound intermediate compound is cleaved from the solid support with a suitable reagent such as TFA resulting in a free amide group which then may be derivatized to achieve compounds of the invention. Alternatively, the B ring may be bound to a carboxyl derivatized support and subsequently coupled to the A ring as shown in Scheme 4.
Scheme 4
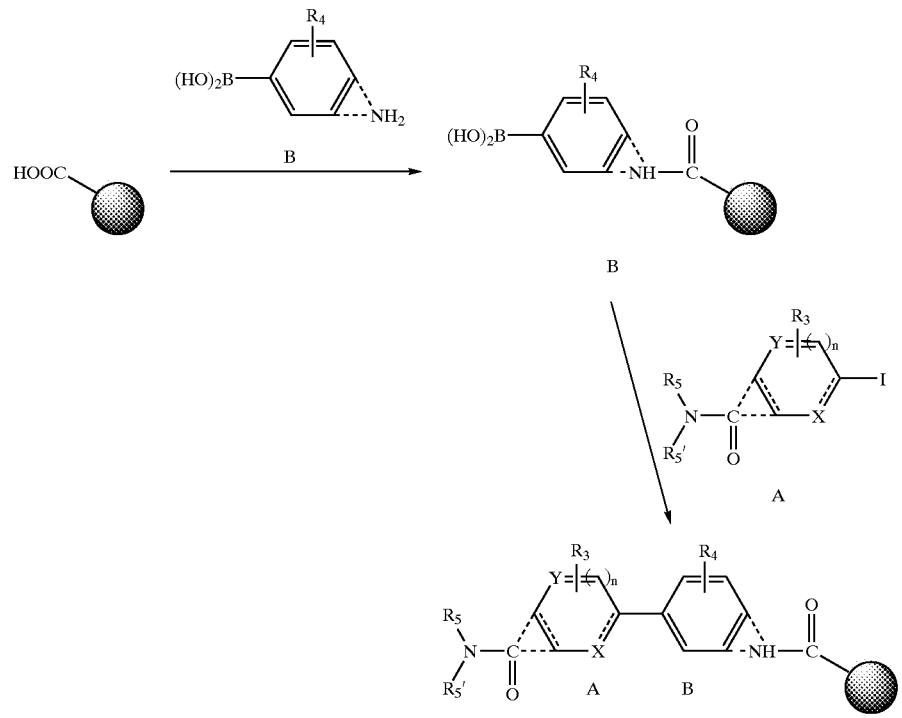

Cleavage from the support by a suitable cleaving reagent such as TEA yields an intermediate with a free amine which may be acylated with a group HOC(O)R$_6$ to yield the desired compound of the invention. It will be appreciated that compounds of the invention may be prepared by solid phase techniques wherein any of the substituent groups R$_3$, R$_4$, R$_5$, R$_{5'}$ and R$_6$ may be bound to the solid support.

In a particularly preferred embodiment, compounds of the invention are prepared by solid phase chemical techniques employing the IRORI MicroKan™ solid phase approach as described by Xiao et al (Biotechnol. Bioeng., 2000, 71(1): 44). MicroKan™ microreactors are rigid containers containing a solid phase resin with mesh side walls in which a single compound is synthesized. Synthesis takes place by allowing reagents to flow through the outer mesh walls of the microreactor using normal laboratory glassware, heating apparatus, cooling apparatus and mixers. Each container further incorporates a miniature radiofrequency (Rf) label for sorting and tracking the particular compound during the synthetic process.

According to an aspect of the invention, there is provided a method of treating bacterial infection in a mammal comprising administering to said mammal, for example a human, an effective amount of a compound of the invention. By "effective amount" is meant an amount of compound which upon administration is capable of reducing or preventing proliferation of the bacteria or reducing or preventing symptoms associated with the bacterial infection. Particular bacteria treatable upon administration of compounds of the invention include *K. pneumoniae, E. coli, S. aureus, E. faecalis* and *M. tuberculosis*. The actual amount of compound administered and the route of administration will depend upon the particular disease or bacteria as well as other factors such as the size, age, sex and ethnic origin of the individual being treated and is determined by routine analysis. In methods of the invention, the compound may be administered orally (including buccal, sublingual, inhalation), nasally, rectally, vaginally, intravenously, intradermally, subcutaneously and topically. Compounds will be formulated into compositions suitable for administration for example with suitable carriers, diluents, thickeners, adjuvants etc as are routine in the formulation art. Compositions of the invention may also include additional active ingredients. Dosage forms include solutions, powders, tablets, capsules, gel capsules, suppositories, topical ointments and creams and aerosols for inhalation.

Formulations for non-parenteral administration may include sterile aqueous solutions which may also contain buffers, diluents and other suitable additives. Pharmaceutically acceptable organic or inorganic carrier substances suitable for non-parenteral administration which do not deleteriously react with compounds of the invention can be used. Suitable pharmaceutically acceptable carriers include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with compounds of the invention. Aqueous suspensions may contain substances which increase the viscosity of the suspension including, for example, sodium carboxymethylcellulose, sorbitol and/or dextran. Optionally, the suspension may also contain stabilizers.

In a preferred embodiment, compounds of the invention are administered via oral delivery. Compositions for oral administration include powders or granules, suspensions or solutions in water or non-aqueous media, capsules, sachets, troches, tablets or SECs (soft elastic capsules or caplets). Thickeners, flavoring agents, diluents, emulsifiers, dispersing aids, carrier substances or binders may be desirably added to such formulations. The use of such formulations has the effect of delivering the nucleic acid to the alimentary canal for exposure to the mucosa thereof. Accordingly, the formulation can consist of material effective in protecting the compound from pH extremes of the stomach, or in releasing the compound over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing formulations for alimentary delivery are well known in the art. See, generally, Nairn, Chapter 83; Block, Chapter 87; Rudnic et al., Chapter 89; Porter, Chapter 90; and Longer et al., Chapter 91 In: *Remington's Pharmaceutical Sciences*, 18th Ed., Gennaro, ed., Mack Publishing Co., Easton, Pa., 1990. The formulations of the invention can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5% to about 95% by weight of the total mixture, i.e., in amounts which are sufficient to achieve the desired dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Compositions may be formulated in a conventional manner using additional pharmaceutically acceptable carriers or excipients as appropriate. Thus, the composition may be prepared by conventional means with additional carriers or excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods well known in the art. The preparations may also contain flavoring, coloring and/or sweetening agents as appropriate.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Formulations of the present invention suitable for oral administration may be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

Furthermore, compounds of the invention may be used as sterilizing agents, for example as an additive or component in scrub solutions for surfaces (i.e., glassware) or in laundering compositions.

EXAMPLE 1

Synthesis of Resins

Synthesis of Amine Resin (2)

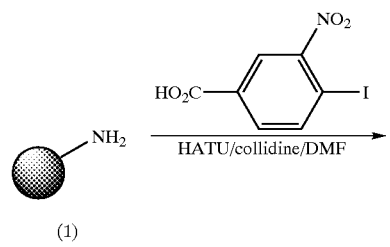

ArgoGel Rink-NH resin (Fmoc-deprotected) (Argonaut Technnologies, San Carlos), (1), was treated with 4-iodo-3-nitrobenzoic acid (0.11 M), collidine (2,3,5-trimethylpyridine) (0.25 M) and HATU (O-1-azabenzotriazol-1-yl)-N,N,N',N'-tetramethylamonium hedxafluorophosphate) (0.11 M) in DMF, overnight at RT. The next day the resin was filtered and washed with DMF, DCM and MeOH.

Synthesis of Proline Resin (4)

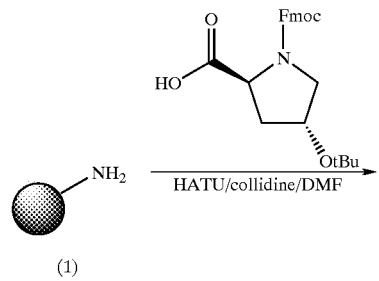

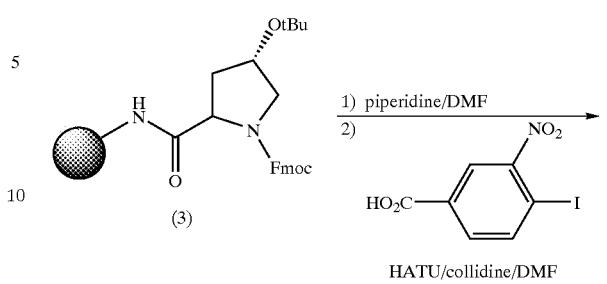

ArgoGel Rink-NH resin (Fmoc-deprotected), (1), was treated with Fmoc-Hyp(OtBu)—OH (0.11 M), collidine (0.25 M) and HATU (0.11 M) in DMF, overnight at RT. The next day the resin was filtered and washed with DMF, DCM and MeOH.

Synthesis of Piperazine Resin (7)

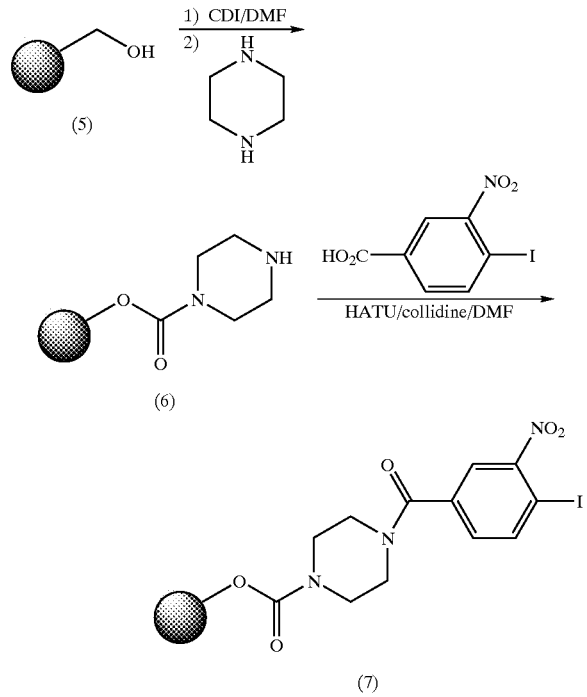

A solution of carbonyldiimidazole (2 equiv, 1.14–33 $10^{-2}$ mol) in DMF was added to ArgoGel Wang resin (5) (15 g, 0.38 mmol, $5.7 \times 10^{-3}$ mmol). The reaction was left swirling over Ar, overnight. The next day the resin was washed with DMF (3×) and DCM (3×). The resin was dried in vacuo. A solution of piperazine (2.45 g, 5 equiv.) in DMF (50 mL) was then added to the resin and the reaction was left swirling overnight, over Ar. The next day the resin was washed with DCM (3×100 mL), DMF (3×100 mL) and MeOH (3×100 mL). The resin was then dried in vacuo. Resin (6) was then treated with 4-iodo-3-nitrobenzoic acid (0.11 M), collidine (0.25 M) and HATU (0.11 M) in DMF, overnight at RT. The next day the resin was filtered and washed with DMF, DCM and MeOH.

EXAMPLE 2
Biaryl Coupling

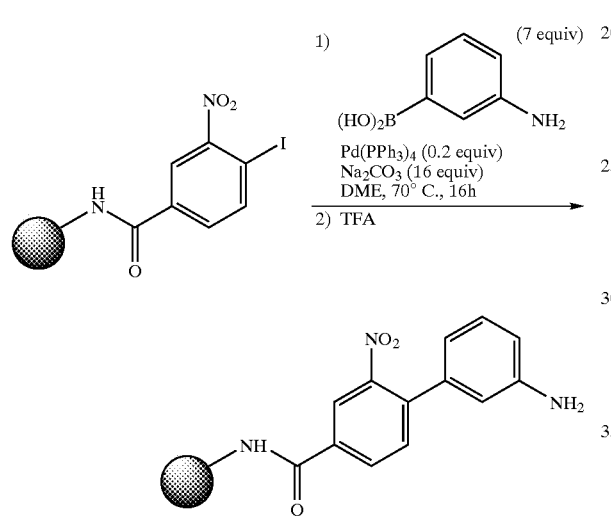

Using the IRORI combinatorial technology, resins (2), (4), and (7) were treated with tetrakistriphenylphosphine palladium (0) (0.017 M in dioxanes, 0.17 equiv.), 3-aminoboronic acid (0.6 M in EtOH, 6 equiv.), aqueous $Na_2CO_3$ (2 M, 13.3 equiv.), and anhydrous ethyleneglycol dimethyl ether (DME). The mixture was swirled and heated overnight at 70° C. under Ar. The next day the mixture was cooled to RT and filtered. The resin was washed with $H_2O$, DME-$H_2O$, DME, $H_2O$, 0.2 N HCl, 1:1 acetic acid-$H_2O$, and neat glacial acetic acid (3×). The resin was then dried in vacuo overnight over $P_2O_5$.

EXAMPLE 3
Acylation of Ring-B Amine

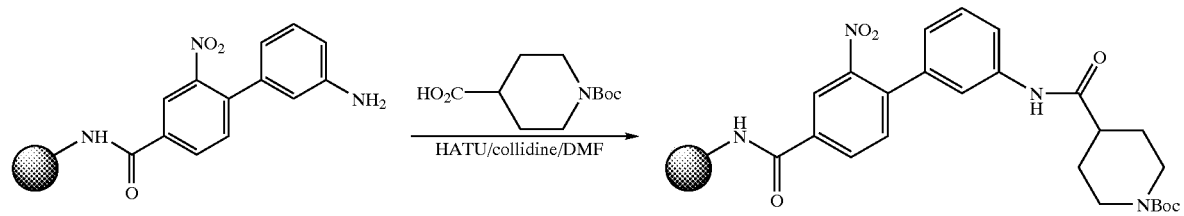

In a typical reaction, the carboxylic acid (0.11 M), HATU (0.11 M) in DMF were added to the reaction flask followed by collidine (0.25 M). For the reaction with 4-methoyxbenzyl isocyanate, a solution of 4-methoxyisocyanate (0.2 M) in DMF was added to the resin under Ar. The reaction was allowed to proceed overnight. The resin was filtered and the washed three times each with DMF, DCM, DMF and MeOH (3×). The resin was dried in vacuo overnight, over $P_2O_5$.

EXAMPLE 4
Nitro Reduction

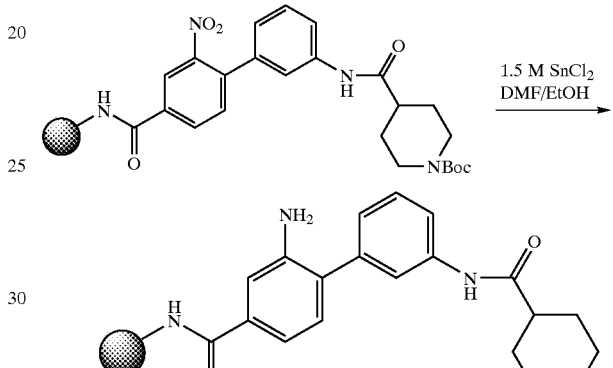

A solution of $SnCl_2$ (1.5) in DMF/EtOH (10:1) was added to the resins. The reaction flask was allowed to swirl overnight, over Ar. The solvent was then removed and the resins washed with IPA, DCM, IPA, $CHCl_3$, DMF and MeOH. The resins were dried in vacuo overnight, over $P_2O_5$.

EXAMPLE 5
Acylation of Ring-A Amine and Cleavage from Resin

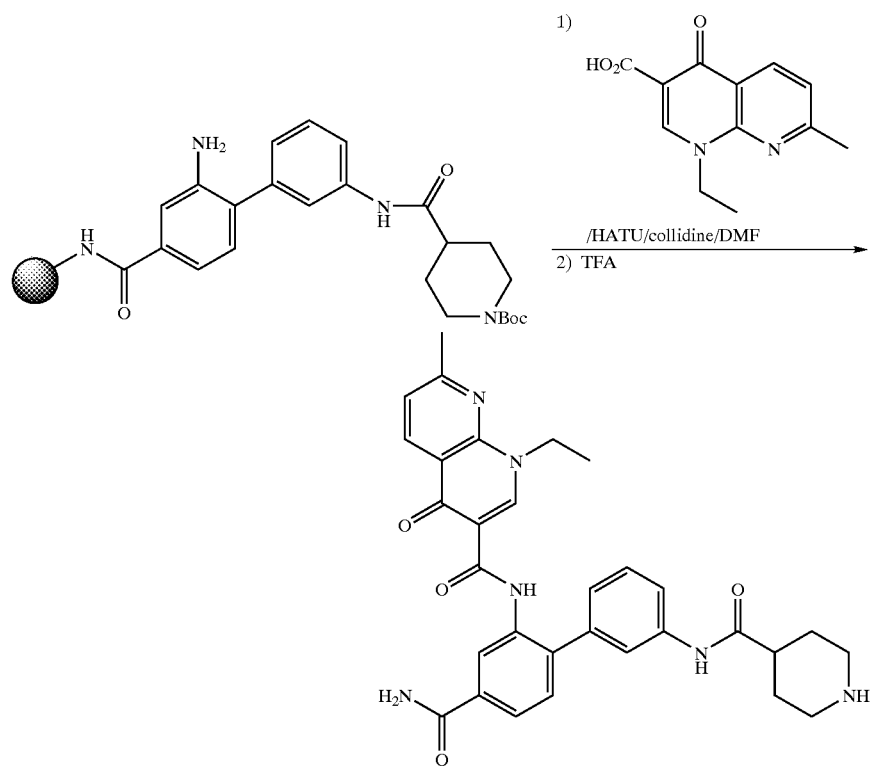

The acylation reactions were carried out in a similar manner to the acylations of the B-ring in example 3. After each MicroKan containing resin was archived into a 96-well plate format, it was washed with 1.8 mL of 95%TFA/5%TIS. The volatiles were removed under vacuum and 500 μL of dioxane/$H_2O$, 1:1 was added to each well. The volatiles were removed under vacuum and the compounds dried under high vacuum, over $P_2O_5$.

TABLE 1

Library members and Analytical Data

| $R_3$[a] | $R_1$ | $R_2$ | HPLC[b] purity (%) | LC-MS (APCI) m/z, (M + H) |
|---|---|---|---|---|
| C | thymine-1-acetyl | hydroxyacetyl | 92 | 565 |
| C | (2S)-2-amino-3-hydroxypropionyl | cytosine-1-acetyl | >95 | 579 |
| A | thymine-1-acetyl | aenine-1-acetyl | >95 | 638 |
| B | 3-(carbamoyl)-benzoyl | cytosine-1-acetyl | >95 | 541 |
| A | hydantoyl | H | >95 | 397 |
| A | adenine-1-acetyl |  | 92 | 559 |
| C | guanine-1-acetyl | cytosine-1-acetyl | 82 | 683 |
| C | 2-pyrazinecarboxyl | hydroxyacetyl | 95 | 505 |
| A | 2,3-dihydroxy-quinoxaline-6-carboxyl | hydroxyacetyl | 77 | 543 |
| B | 3-(carbamoyl)-benzoyl | H | >95 | 390 |

TABLE 1-continued

Library members and Analytical Data

| $R_3$[a] | $R_1$ | $R_2$ | HPLC[b] purity (%) | LC-MS (APCI) m/z, (M + H) |
|---|---|---|---|---|
| C | 2-pyrazinecarboxyl | thymine-1-acetyl | >95 | 613 |
| B | isonipecotyl | cytosine-1-acetyl | >95 | 490 |
| B | adenine-1-acetyl | hydroxyacetyl | 85 | 461 |
| A | 1-aminoacetyl | thymine-1-acetyl | 97 | 520 |
| A | hydroxyacetyl | (2S)-2-amino-3-hydroxypropionyl | 93 | 442 |
| A | 2-pyrazinecarboxyl | 1-aminoacetyl | >95 | 460 |
| A | 2,3-dihydroxy-quinoxaline-6-carboxyl | thymine-1-acetyl | 77 | 651 |
| C | 2-pyrazinecarboxyl | H | >95 | 447 |
| B | (2S)-2-amino-3-hydroxypropionyl | hydroxyacetyl | 92 | 373 |
| C | hydantoyl | (2S)-2-amino-3-hydroxypropionyl | >95 | 528 |

[a]A = piperazinecarboxyl; B = aminoformyl; C = (4S)-2-carbomoyl-4-hydroxypyrrolidinecarboxyl
[b]RP-HPLC equipped with a light scattering detector

EXAMPLE 6

Attaching Heteroaryl A-rings to Resins

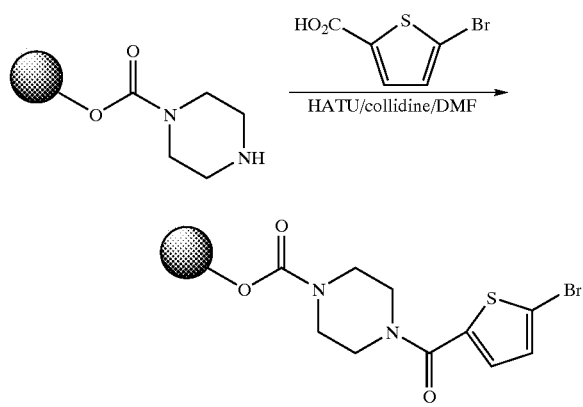

Proline and piperazine resins prepared in example 1 were treated with 20% piperidine/DMF for 30 min. The resins were then washed with DMF, DCM and MeOH and dried under high vacuum over $P_2O_5$. The deprotected resins were reacted with 6-bromopicolinic acid, 5-bromofuroic acid, 5-bromonicotonic acid or 5-bromothiophene-2-carboxylic acid (shown) (0.11 M), HATU (0.11 M) and collidine (0.25 M) in DMF. The reactions were left stirring overnight, at RT. The next day the resins were filtered and washed with DMF, DCM and MeOH.

EXAMPLE 7
Suzuki Coupling to Heteroaryl A-ring

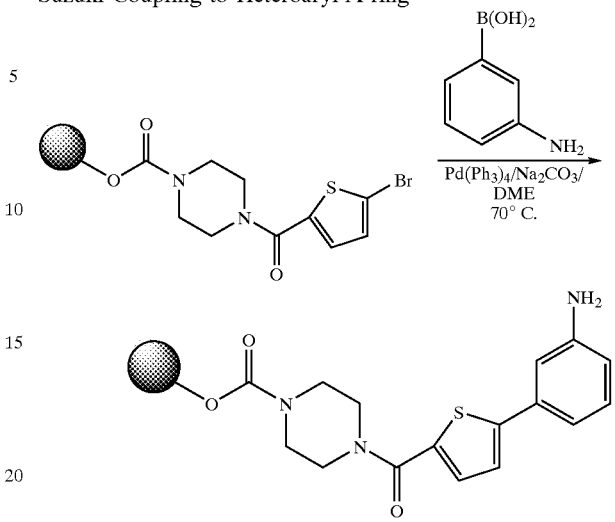

Each of resins with a heteroaryl A-ring were combined and treated with tetrakistriphenylphosphine palladium (0) (0.017 M in dioxanes, 0.17 equiv.), 3-aminoboronic acid (0.6 M in EtOH, 6 equiv.), aqueous $Na_2CO_3$ (2 M, 13.3 equiv.), and anhydrous ethyleneglycol dimethyl ether (DME). The mixture was swirled and heated overnight at 70° C. under Ar. The next day the mixture was cooled to RT and filtered. The resin was washed with $H_2O$, DME-$H_2O$, DME, $H_2O$, 0.2 N HCl, 1:1 acetic acid-$H_2O$, and neat glacial acetic acid (3× each). The resin was then dried in vacuo overnight over $P_2O_5$.

EXAMPLE 8
Acylation of Compounds with Heteroaryl A-ring

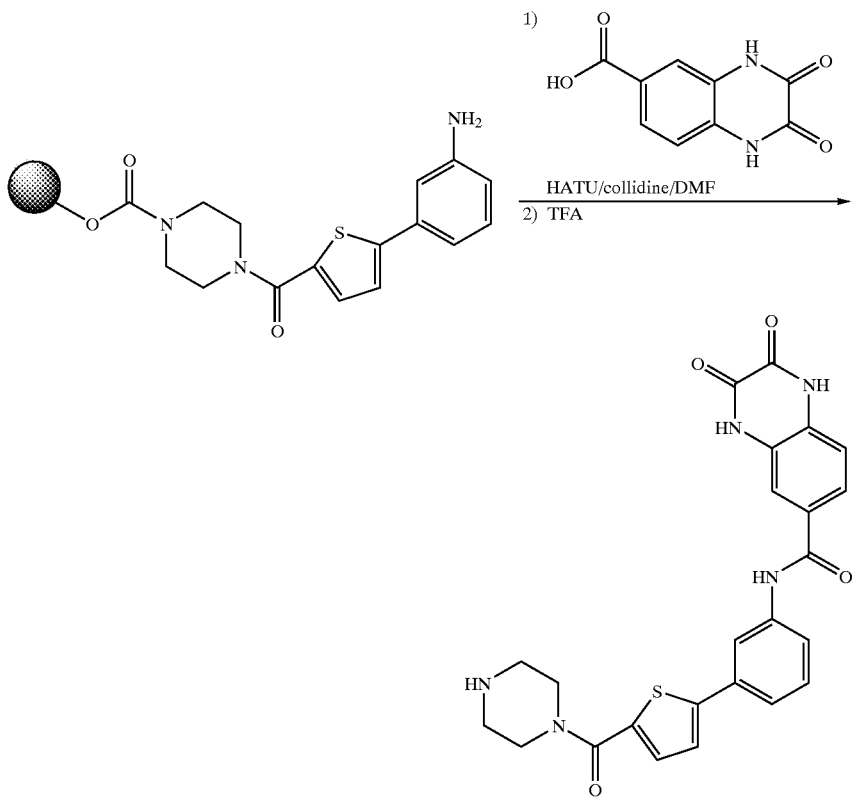

The carboxylic acid (0.11 M), HATU (0.11 M) and DMF were added to the reaction flask followed by collidine (0.25 M). The resin was then added to this solution and the reaction allowed to proceed overnight, over Ar. The resin was filtered and the washed with DMF, DCM, DMF and MeOH (3× each). The resin was dried in vacuo overnight, over $P_2O_5$. After each MicroKan containing resin, was archived into a 96-well plate format, it was washed with 1.8 mL of 95%TFA/5%TIS. The volatiles were removed under vacuum and 500 μL of dioxane/$H_2O$, 1:1 was added to each well. The volatiles were removed under vacuum and the compounds dried under high vacuum, over $P_2O_5$.

TABLE 2

Analytical Data for Heterobiaryl Library

| Library Member | MS-EI, m/z (M + H) | Purity (%)[a] |
|---|---|---|
| 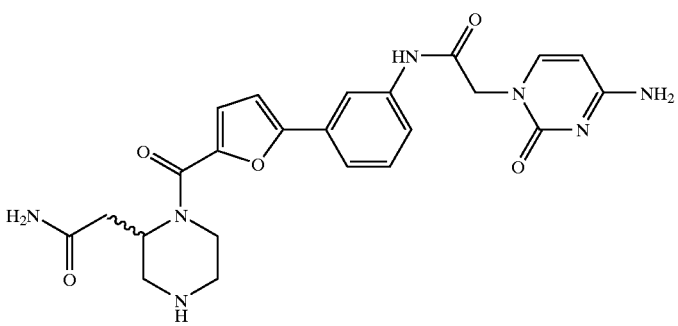 | 480 | >95 |
| 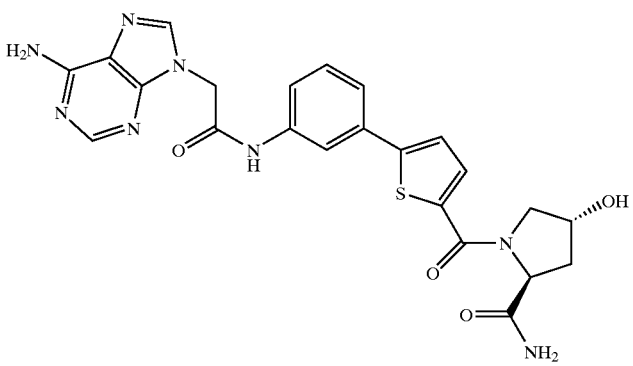 | 507 | >95 |
| 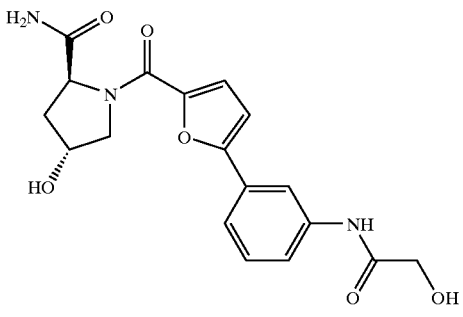 | 374 | 89 |
| 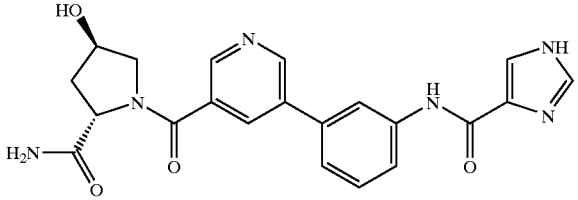 | 421 | >95 |

TABLE 2-continued
Analytical Data for Heterobiaryl Library
| Library Member | MS-EI, m/z (M + H) | Purity (%)[a] |
|---|---|---|
| 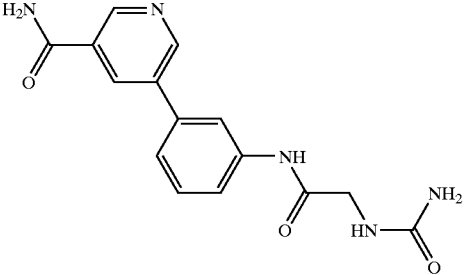 | 314 | 87 |
| 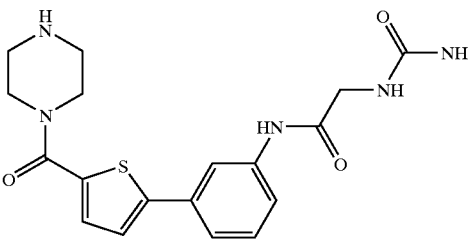 | 388 | >95 |
| 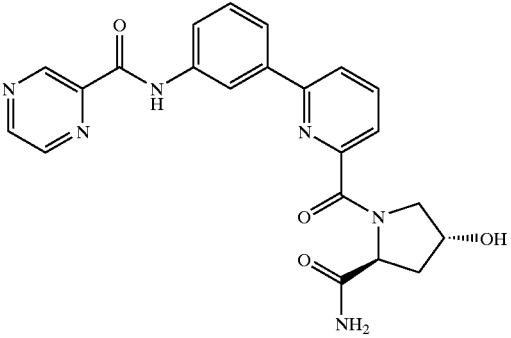 | 433 | >95 |
| 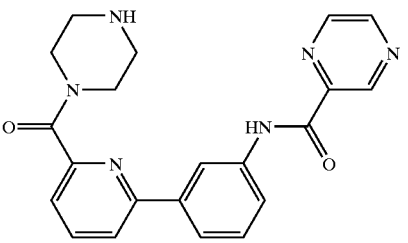 | 389 | 88 |
| 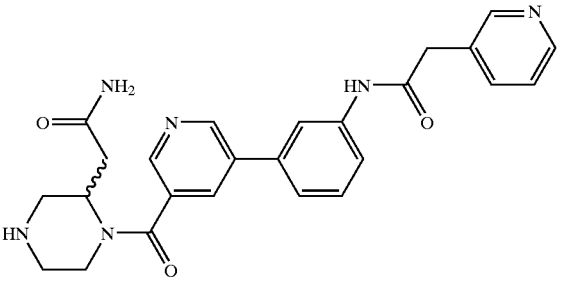 | 459 | >95 |

TABLE 2-continued

Analytical Data for Heterobiaryl Library

| Library Member | MS-EI, m/z (M + H) | Purity (%)[a] |
|---|---|---|
| (structure) | 322 | >95 |
| (structure) | 482 | >95 |
| (structure) | 479 | 91 |
| (structure) | 443 | >95 |
| (structure) | 330 | >95 |

[a]Purity determined by RP-HPLC using an evaporative light scattering detector.

a) Purity determined by RP-HPLC using an evaporative light scattering detector.

EXAMPLE 9
Heteroaryl Compounds with Amino Acid Spacer

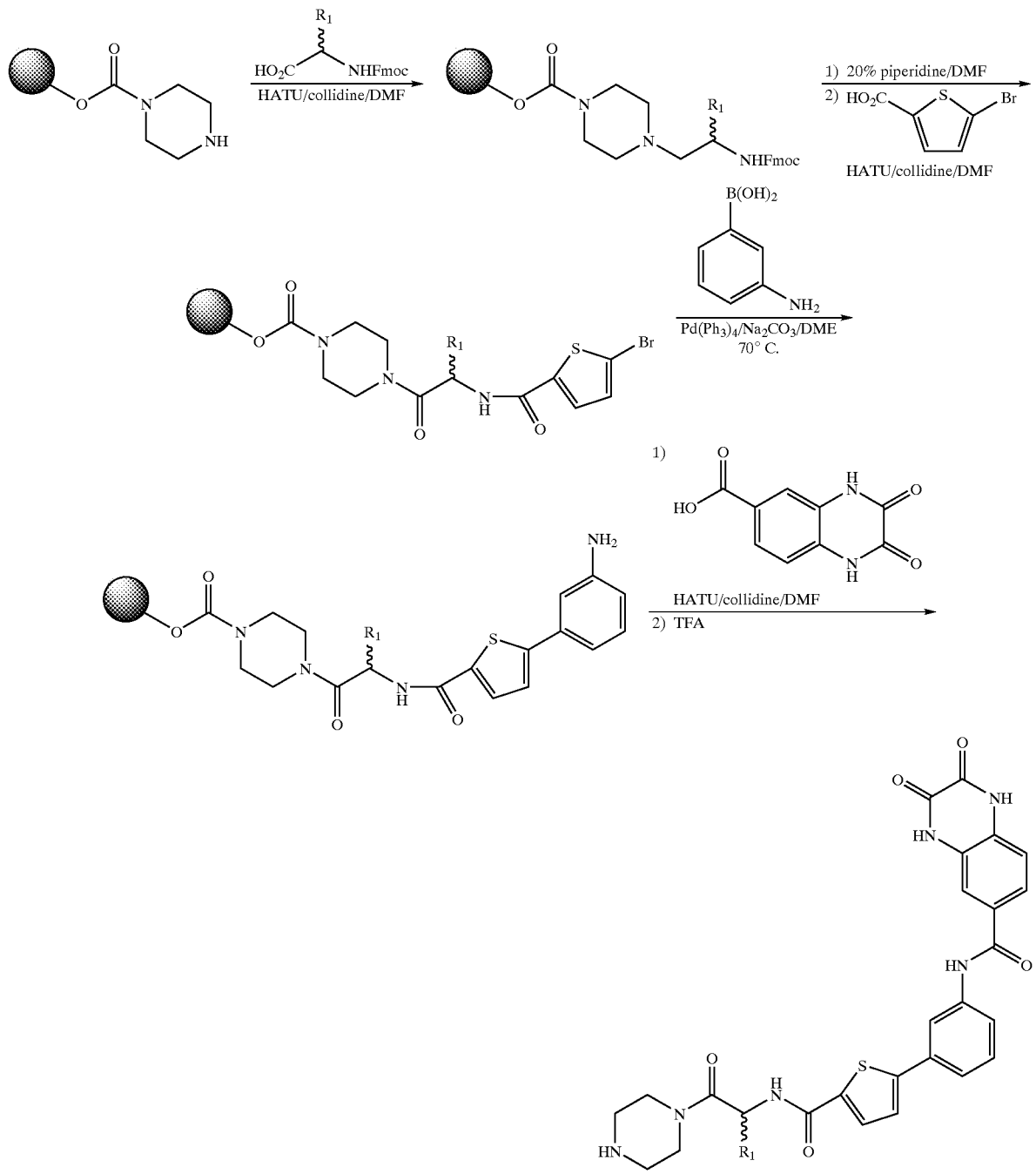

An amino acid spacer library was prepared according to Scheme 5. An amino acid was coupled directly to the piperazine resin. The resin was then Fmoc-deprotected and reacted with 5-bromothiophene-2-carboxylic acid. A Suzuki coupling reaction was carried out with 3-aminophenylboronic acid and the arylamine acylated with 2,3-dihydroxyquinoxaline-6-carboxylic acid.

EXAMPLE 10
In Vitro Antibacterial Activity

Bacterial Strains. The *Streptococcus pyogenes* strains, *Klebsiella pneumoniae, Escherichia coli, Staphylococcus aureus, Enterococcus faecalis* used in the antibacterial activity studies ATCC 14289, 49399, 13883, 25922, 13709, 29212, respectively, are obtained from the American Type Culture Collection, Rockville, Md. The strain *E. coli* imp- is a mutant strain of wild type *E. coli* with increased outer membrane permeability and was grown in LB broth at 37° C. S. pyogenes strain is grown in Todd-Hewitt broth. S.

*aureus* is grown in trypticase soy broth, *E. faecalis* in Todd-Hewitt broth, wild type *E. coli* and *K. pneumoniae*, in nutrient broth.

Determination of Minimum Inhibitory Concentrations (MICs). The assays were carried out in 150 L volume in duplicate in 96-well clear flat-bottom plates. The bacterial suspension from an overnight culture growth in appropriate medium was added to a solution of test compound in 4% DMSO in water. Final bacterial inoculum was approximately $10^5$–$10^6$ CFU/well. The percent growth of the bacteria in test wells relative to that observed for a well containing no compound was determined by measuring absorbance at 595 nm ($A_{595}$) after 24 h. The MIC was determined as a range of single compound where the complete inhibition of growth was observed at the higher concentration and cells were viable at the lower concentrations. Both ampicillin and tetracycline is used as antibiotic-positive controls in each screening assay for *S. pyogenes*, *E. coli* imp-, *E. coli*, *S. aureus*, *E. faecalis*, *K pneumoniae* and *P. vulgaris*. Ciprofloxacin is used as an antibiotic positive control in each screening assay for *P. aeruginosa*.

Mass-spec Binding Assays.

Binding affinity of test compounds to a 58 nucleotide fragment of *E. coli* 23S ribosomal RNA (23S rRNA) was determined using electrospray ionization Fourier transform ion cyclotron resonance mass spectrometry (ESI-FTICR-MS). The structure of the 23S rRNA fragment and its preparation is described by Conn et al (Science, 1999, 284(5417):1171) and Hinck et al (J. Mol. Biol., 1997, 274(1): 101) both incorporated herein by reference. The mass spec assay determined the exact chemical composition of ligands that bound to the target rRNA and determined relative or absolute dissociation ($K_D$) of ligands for the target. In the first step of the assay, a mixture of 23S rRNA target and test compound were moved from solution into the gas phase by electrospray ionization. The FT-ICR mass spectrometer served as a parallel set of "scales", simultaneously measuring the exact molecular masses of the small molecules that bound to the RNA with great accuracy. The mass measurement error for an RNA-ligand complex weighing 10 kDa equals the mass of an electron. At this level of mass accuracy, each compound in the mixture was "labeled" by its molecular formula and exact molecular mass. The assay was performed using standard 96-well plates with robotic liquid handlers to transfer mL amounts of sample into the mass spectrometer and was run with solutions containing magnesium and 200 mM ammonium acetate buffer to aid RNA folding, and 2% DMSO to dissolve potential ligands.

Animals and In Vivo studies. Male ICR mice are fed with autoclaved commercial food pellets and sterile water ad libitum. Animals are inoculated intraperitoneally with 8.0× $10^6$ CFU/0.5 mL/mouse of *K. pneumoniae* (ATCC 10031) in BHI containing 5% mucin. Ten animals each are randomly assigned to either control or treatment groups. Test compound (DMSO solution, 100 mg/kg, 33.3 mg/kg and 3.3 mg/kg) and gentamycin (3 mg/kg, included as a positive control) are both administered subcutaneously one hour after infection. Test compound is administered as a solution in DMSO (100%) and 50 µL/mouse while gentamycin is administered as an aqueous buffer solution (phosphate buffered saline (PBS), pH=7.4).

Coupled Bacterial Transcription/Translation Assay. The DNA template, pBestLuc™ (Promega), is a plasmid containing a reporter gene for firefly luciferase fused to a strong tac promoter and ribosome binding site. Messenger RNA from 1 µg pBestLuc was transcribed and translated in *E. coli* S30 bacterial extract in the presence or absence of test compound. Compounds were tested in a black 96 well microtiter plate with an assay volume of 35 µL. Each test well contained: 5 µL test compound, 13 µL S30 premix (Promega), 4 µL 10× complete amino acid mix (1 mM each), 5 µL *E. coli* S30 extract and 8 µL of 0.125 µg/µL pBestLuc™. The transcription/translation reaction was incubated for 35 minutes at 37° C. followed by detection of functional luciferase with the addition of 30 µL LucLite™ (Packard). Light output was quantitated on a Packard Top-Count.

Amino Acid Misincorporation Assay. A mutant form of ubiquitin devoid of the amino acid tyrosine was produced in vitro in *E. coli* S-30 extracts in the presence of a tritiated tyrosine. Since ubiquitin has no tyrosine in the sequence, if tyrosine is used as the labeled amino acid, any incorporated counts above background is assumed to be due to the misincorporation of the tritiated amino acid. The labeled protein is captured via a ubiquitin antibody which is associated with anti-rabbit SPA beads. Altered ubiquitin molecules are not efficiently captured by the antibody. Compounds are tested in 96 well microtiter plate in an assay volume of 10 µL. Control experiments using the antibiotics, kanamycin, novabiocin, monensin, gentamicin, neomycin, tetracycline are run at 5 µM of each antibiotics. Test compounds are tested at 5 µM, 50 µM, and 500 µM.

Results of biological activity assays of biaryl compounds of the invention are summarized in tables 3–6.

TABLE 3

Biological activity of biaryl compounds

| R group on A-ring | Translation $IC_{50}$ (µmol) | *E. coli* MIC (µM) | 23S RNA Affinity Kd (µM) |
|---|---|---|---|
| (quinoxalinedione) | | | 75 |
| (thiophene) | | | 50 |
| (2-aminothiazole) | | | 50 |
| (pyridine) | | | 100 |

TABLE 3-continued

Biological activity of biaryl compounds

| R group on A-ring | Translation IC$_{50}$ ($\mu$mol) | E. coli MIC ($\mu$M) | 23S RNA Affinity Kd ($\mu$M) |
|---|---|---|---|
| (1,8-naphthyridinone with N-ethyl, methyl) | 35 | 50 | |
| (guanine) | 80 | | |
| (pyridin-3-yl) | 100 | | |
| (cytosin-1-yl) | >100 | >100 | 130 |

TABLE 4

Heteroaryl compounds

| Heteroaryl compound | Translation IC$_{50}$ ($\mu$mol) |
|---|---|
| (quinoxalinedione-carboxamide-phenyl-thiophene-piperazine structure) | 25 |

TABLE 4-continued

Heteroaryl compounds

| Heteroaryl compound | Translation IC$_{50}$ ($\mu$mol) |
|---|---|
| [structure: quinoxaline-2,3-dione-carboxamide-phenyl-furan-piperazinyl ketone] | 25 |
| [structure: quinoxaline-2,3-dione-carboxamide-phenyl-(X)-thiophene-piperazinyl ketone] | 25 |
| [structure: quinoxaline-2,3-dione-carboxamide-phenyl-thiazole-piperazinyl ketone] | 75 |
| [structure: pyridine-phenyl-quinoxaline-2,3-dione carboxamide with piperazinyl ketone] | — |

TABLE 4-continued
Heteroaryl compounds
| Heteroaryl compound | Translation IC$_{50}$ ($\mu$mol) |
|---|---|
| 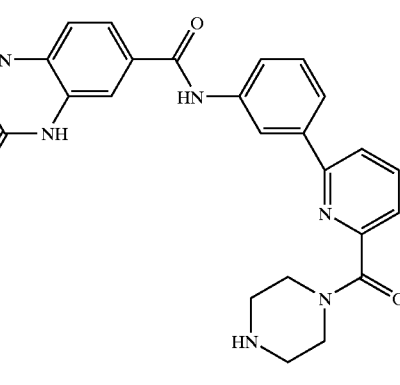 | — |
| 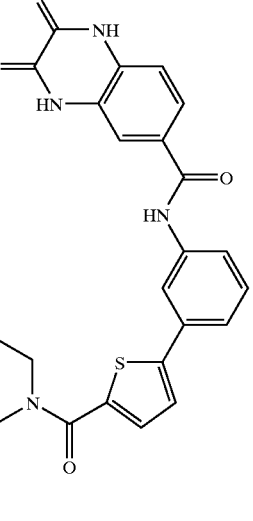 | 25 |
| 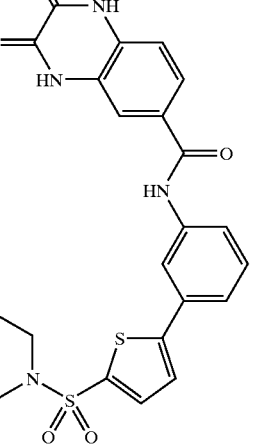 | 35 |

TABLE 4-continued

Heteroaryl compounds

| Heteroaryl compound | Translation IC$_{50}$ ($\mu$mol) |
|---|---|
| (structure) | 80 |
| (structure) | 80 |
| (structure) | 55 |

TABLE 4-continued
Heteroaryl compounds
| Heteroaryl compound | Translation IC$_{50}$ ($\mu$mol) |
|---|---|
| 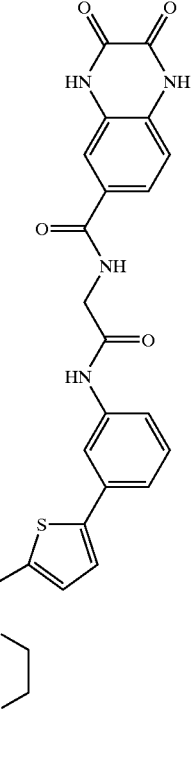 | 100 |
| 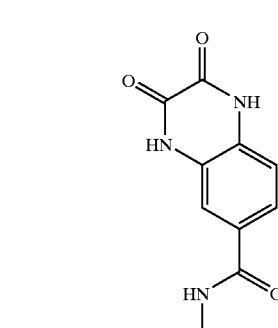 | 25 |

TABLE 4-continued

Heteroaryl compounds

| Heteroaryl compound | Translation IC$_{50}$ (μmol) |
|---|---|
| [structure] | — |
| [structure] | 50 |
| [structure] | 30 |

TABLE 4-continued

Heteroaryl compounds

| Heteroaryl compound | Translation IC$_{50}$ ($\mu$mol) |
|---|---|
| [structure] | 25 |

TABLE 5

Heteroaryl Compounds with Amino Acid Spacer

[structure 1]

TABLE 5-continued

Heteroaryl Compounds with Amino Acid Spacer

[structure 2]

TABLE 5-continued
Heteroaryl Compounds with Amino Acid Spacer
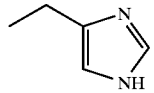
| Structure, R= | approx. $K_d$ ($\mu$mol) | Translation $IC_{50}$ ($\mu$mol) |
|---|---|---|
| 1 | 79 | 25 |
| 2, H | 86 | 20 |
| 3 | 139 | 35 |
| 2, 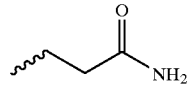 | 61 | 12 |
| 2, 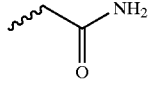 | 45 | 40 |
| 2, 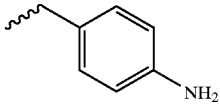 | 46 | 25 |
TABLE 5-continued
Heteroaryl Compounds with Amino Acid Spacer
| | | |
|---|---|---|
| 2, 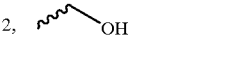 | 100 | 12 |
| 2, | 143 | 45 |
| 2, | 142 | 50 |
| 2, | 36 | 35 |
| 2, | N/A | 55 |
| 2, | 122 | 60 |
| 2, | 135 | 60 |
TABLE 6
Heteroaryl Compounds
| Compound | MIC ($\mu$M) |
|---|---|
| 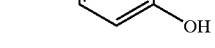 | S. pyogenes 25–50<br>S. aureus 50–100<br>E. hirae 50–100<br>E. coli 50–100<br>K. pneumoniae 50–100 |

TABLE 6-continued

Heteroaryl Compounds

| Compound | | MIC (μM) |
|---|---|---|
| 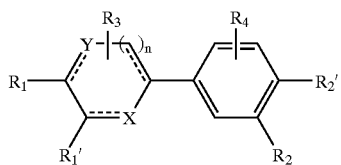 | S. pyrogenes | 50–100 |
| | S. pyrogenes | 50–100 |
| | E. coli | 50–100 |

Those skilled in the art will appreciate that numerous changes and modifications may be made to the preferred embodiments of the present invention, and that such changes and modifications may be made without departing from the spirit of the invention. It is, therefore, intended that the spirit and scope of the appended claims should not be limited to the description of the preferred embodiments contained herein, but, that the appended claims cover all such equivalent variations as fall within the true spirit and scope of the invention.

We claim:

1. A compound having the formula I:

I wherein:

X is O or S;

Y is CH;

n is 0;

one of $R_1$ and $R_{1'}$ is —C(O)$NR_5R_{5'}$, —C(O)—Q—$NR_5R_{5'}$, —$CH_2NR_5R_{5'}$ or —S(O)$_2NR_5R_{5'}$ and the other is $R_3$;

one of $R_2$ and $R_{2'}$ is —NHC(O)$R_6$ or —NHS(O)$_2R_6$ and the other is $R_4$;

Q is an amino acid or peptide;

$R_3$ is —$NR_5R_{5'}$;

$R_4$ is selected from the group consisting of H, halogen, hydroxyl, amino, carboxyl, alkyl, alkenyl, alkynyl, alkoxy, a carbocycle radical and a heterocycle radical;

$R_5$ is selected from the group consisting of H and alkyl optionally substituted with an amino, hydroxyl or urea radical;

$R_{5'}$ is H; and $R_6$ is selected from the group consisting of H; amino; alkyl, alkenyl or alkynyl, each optionally substituted with halogen, amino, amidinyl, guanidinyl, urea radical, carboxyl or carboxamide radical; a 5–16 member carbocycle radical or heterocycle radical; and a 5–16 member heterocycle-substituted alkyl or carbocycle-substituted alkyl, wherein said carbocycle radical and heterocycle radical are optionally substituted with halogen, OH, amino, alkyl, carboxyl, oxo or carboxamide radical.

2. A compound according to claim 1, wherein $R_{5'}$ is H and $R_5$ is aminomethyl, hydroxymethyl, or ureamethyl.

* * * * *

UNITED STATES PATENT AND TRADEMARK OFFICE
CERTIFICATE OF CORRECTION

PATENT NO.         : 6,849,660 B1
APPLICATION NO. : 09/630122
DATED                  : February 1, 2005
INVENTOR(S)       : Elizabeth Jefferson et al.

It is certified that error appears in the above-identified patent and that said Letters Patent is hereby corrected as shown below:

1) Title Page:
Item [56], References Cited, OTHER PUBLICATIONS, "Ehmer" reference, please delete "PH450c17" and insert therefor -- P450c17 --;

UNITED STATES PATENT AND TRADEMARK OFFICE
CERTIFICATE OF CORRECTION

PATENT NO. : 6,849,660 B1
APPLICATION NO. : 09/630122
DATED : February 1, 2005
INVENTOR(S) : Elizabeth Jefferson et al.

It is certified that error appears in the above-identified patent and that said Letters Patent is hereby corrected as shown below:

2) Title Page:
Item [57], Abstract, please delete "Provided are antibacterial compounds having Formula I:

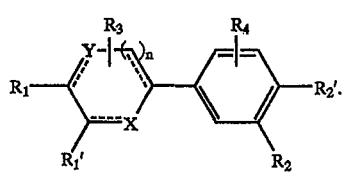

I

In such compositions, X is O or S; Y is $CH_2$; n is 0 or 1. One of $R_1$ and $R_{1'}$ is $-C(O)NR_5R_{5'}$, $-C(O)-Q-NR_5R_{5'}$, $CH_2NR_5R_{5'}$ or $-S(O)_2NR_5R_{5'}$ and the other is H or $R_3$. One of $R_2$ and $R_{2'}$ is $-NHC(O)R_6$ or $-N-CHS(O)_2R_6$ and the other is H or $R_4$. Q is an amino acid or peptide. $R_3$ is H, halogen, $-NR_5R_{5'}$ or $-NHC(O)R_6$; and $R_4$ is selected from the group consisting of H, halogen, hydroxyl, amino, carboxyl, alkyl, alkenyl and alkynyl. $R_5$ is selected from the group consisting of H, alkyl, alkenyl or alkynyl optionally substituted with halogen, OH, amino amidinyl, guanidinyl, urea, alkyl, carboxyl, oxo, carboxamide; $R_{5'}$ is H or $R_5$ and $R_{5'}$ together form a 5-16 member heterocycle optionally substituted with halogen, OH, amino, alkyl, carboxyl, carbonyl or carboxamide. R6 is selected from the group consisting of H; amino; alkyl, alkenyl or alkynyl, each optionally substituted with halogen, amino, amidinyl, guanidinyl, urea, carboxyl or carboxamide; a 5-16 member carbocycle or heterocycle; and a 5-16 member heterocycle-substituted alkyl or carbocycle-substituted alkyl, wherein said carbocycle and heterocycle are optionally substituted with halogen, OH, amino, alkyl, carboxyl, oxo or carboxamide"

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,849,660 B1 | Page 1 of 1 |
| APPLICATION NO. | : 09/630122 | |
| DATED | : February 1, 2005 | |
| INVENTOR(S) | : Elizabeth Jefferson et al. | |

It is certified that error appears in the above-identified patent and that said Letters Patent is hereby corrected as shown below:

Column 1, line 2, please insert

-- STATEMENT OF FEDERALLY SPONSORED RESEARCH

This work reported was made with United States Government support under DARPA contract N65236-99-1-5419. The United States Government may have certain rights to the invention.--.

Signed and Sealed this

Second Day of October, 2007

JON W. DUDAS
*Director of the United States Patent and Trademark Office*